United States Patent [19]

Bedford et al.

[11] Patent Number: 4,567,278
[45] Date of Patent: Jan. 28, 1986

[54] PROCESS FOR RACEMIZING CERTAIN SPIRO COMPOUNDS

[75] Inventors: Geoffrey R. Bedford, Congleton; David R. Brittain, Rochdale; Ronald Platt, MacClesfield, all of United Kingdom

[73] Assignee: Imperial Chemical·Industries PLC, United Kingdom

[21] Appl. No.: 593,312

[22] Filed: Mar. 26, 1984

[51] Int. Cl.⁴ .......................................... C07D 487/10
[52] U.S. Cl. .................................... 548/309; 548/410
[58] Field of Search ................. 548/309, 410; 562/401

[56] References Cited

U.S. PATENT DOCUMENTS

| | | | |
|---|---|---|---|
| 2,743,284 | 4/1956 | Klein et al. | 549/319 |
| 3,024,231 | 3/1962 | Scherrer | 260/239.3 A |

FOREIGN PATENT DOCUMENTS

| | | | |
|---|---|---|---|
| 0028906 | 5/1981 | European Pat. Off. | 548/309 |
| 0065407 | 11/1982 | European Pat. Off. | 548/410 |
| 1569486 | 6/1980 | United Kingdom | 546/242 |

OTHER PUBLICATIONS

Gilman, H., et al. (Editors), *Organic Chemistry*, John Wiley, New York, 1938, pp. 176–177.
Gilman, H., et al. (Editors), *Organic Chemistry*, Second Edition, John Wiley, New York, 1943, pp. 241–248.
H. Matsuo, et al., *Chem. Pharm. Bull.*, 1967, 15(4), 391–398.
T. Fukumura, *Agric. Biol. Chem.*, 1977, 41(8), 1327–1330.
T. Fukumura, et al., *FEBS Letters*, 1978, 89 (2), 298–300.
I. Z. Siemon, et al., *Z. fur Naturforeschung*, 1971, 26, 762–764.
V du Vigneaud, et al., *J. Biol. Chem.*, 1932, 99, 143.

*Primary Examiner*—Richard A. Schwartz
*Attorney, Agent, or Firm*—Cushman, Darby & Cushman

[57] ABSTRACT

The invention concerns a novel process for the racemisation of unwanted enantiomeric forms of 1′-substituted spiro[imidazolidine-4,3′-indoline]-2,2′,5-triones and 1′-substituted spiro[pyrrolidine-3,3′-indoline]-2,2′,5-triones which comprises heating an unwanted enantiomeric form (or a mixture containing an excess of one enantiomer over the other) alone or, more conveniently, in the presence of a solvent or diluent at a temperature in the range 80° to 280° C.

9 Claims, No Drawings

PROCESS FOR RACEMIZING CERTAIN SPIRO COMPOUNDS

This invention relates to a chemical process and more particularly, it relates to a chemical process for the production of various spiro-linked tricyclic heterocyclic compounds in racemic form from their corresponding optically active forms.

It is known from our earlier publications that certain 1'-substituted spiro[imidazolidine-4,3'-indoline]-2,2',5-triones (European patent application, publication No. 28906A1) and 1'-substituted spiro[pyrrolidine-3,3'-indoline-2,2',5-triones (European patent application, publication No. 65407A2) are potent inhibitors of the enzyme aldose reductase and are of use in the reduction or prevention of the development of certain complications of protracted diabetes or galactosemia. These spiro-linked tricyclic heterocyclic compounds contain an asymmetric carbon atom (the spiro-linking carbon) and exist (and may be isolated) as two individual optically active forms (individual enantiomers) or mixtures thereof. The mixture containing equal amounts of both enantiomers is optically inactive and is known as the racemic form or racemate. The latter form is normally obtained by chemical syntheses which do not involve optically active starting materials.

In many cases it is possible to increase on the potency of the racemic form by separating out the individual optically active forms (individual enantiomers), that is one enantiomer may possess significantly greater potency as an inhibitor of the enzyme aldose reductase than does the other enantiomer. Such a separation of a racemic form is well known in the chemical art and is known as resolution and permits the production of both enantiomers. However, as stated above, in practice only one enantiomer may possess significant aldose reductase inhibitory properties. It is consequently desirable in any large-scale process for resolution of a racemic form to be able to convert the unwanted enantiomer into the racemic form again. We have now discovered, and herein lies the basis for our invention, that individual enantiomers of the above mentioned spiro-linked tricyclic heterocyclic compounds can be unexpectedly converted to the corresponding racemic form merely by the influence of heat.

According to the invention there is provided a process for the manufacture of a compound of the formula I (set out hereinafter) in racemic form, wherein Ra is (2–12C)alkyl, or naphthylmethyl or cinnamyl optionally bearing one or two halogeno substituents, or benzyl optionally bearing one or two substituents independently selected from halogen, (1–4C)alkyl, (1–4C)alkoxy, cyano, nitro and trifluoromethyl located in the 2-, 3-, 4- or 5-position of the phenyl moiety; benzene ring A optionally bears one or two substituents independently selected from halogeno, (1–4C)alkyl, trifluoromethyl and nitro; and Q is methylene or imino; but Ra is other than ethyl, n-propyl or unsubstituted benzyl when benzene ring A is unsubstituted and Q is imino; characterised by heating an enantiomeric form of the compound of formula I; or a mixture of both enantiomeric forms of said compound containing an excess of one enantiomeric form over the other; at a temperature in the range 80° to 280° C.

A particular value for Ra when it is (2–12C)alkyl is, for example, ethyl, propyl, butyl, pentyl, hexyl, heptyl, nonyl or decyl.

A particular value for Ra when A is naphthylmethyl or cinnamyl bearing one or two halogeno substituents is, for example, 5-chloro-1-naphthylmethyl, 6-chloro-2-naphthylmethyl or 3,4-dichlorocinnamyl.

Particular values for optional substituents on benzene ring A or as part of Ra are by way of example:
for (1–4C)alkyl: methyl or ethyl;
for (1–4C)alkoxy: methoxy or ethoxy; and
for halogeno; fluoro, chloro, bromo or iodo.

A particular compound of formula I may be obtained in racemic form by the process of the invention by heating an enantiomeric form of a compound of the formula I wherein Ra is a propyl, butyl, pentyl, hexyl, heptyl, 1-naphthylmethyl, 2-naphthylmethyl, cinnamyl, halogenocinnamyl (especially 4-chlorocinnamyl), dihalogenocinnamyl (especially 3,4-dichlorocinnamyl), benzyl, (1–4C)alkylbenzyl (especially 4-methylbenzyl), trifluoromethyl- or halogeno-benzyl [especially 3-(trifluoromethyl)benzyl, 4-(trifluoromethyl)benzyl, 4-chlorobenzyl or 4-bromobenzyl], or dihalogenobenzyl (especially 2,4-dichlorobenzyl, 4-chloro-2-fluorobenzyl, 4-bromo-2-fluorobenzyl, 2-fluoro-4-iodobenzyl, 3,4-dichlorobenzyl, 3-bromo-4-chlorobenzyl or 4-bromo-3-chlorobenzyl); benzene ring A is unsubstituted or bears a fluoro, chloro, bromo, methyl or trifluoromethyl substituent located at the 5'-, 6'- or 7'-position; and Q is imino or methylene; but Ra is other than ethyl, n-propyl or unsubstituted benzyl when benzene ring A is unsubstituted and Q is imino.

One group of racemic forms of compounds of the formula I for which the process of the invention is especially suitable, comprises those compounds wherein Ra is dihalogenobenzyl (especially 2,4-dichlorobenzyl, 4-chloro-2-fluorobenzyl, 4-bromo-2-fluorobenzyl, 2-fluoro-4-iodobenzyl, 3,4-dichlorobenzyl, 3-bromo-4-chlorobenzyl or 4-bromo-3-chlorobenzyl) and benzene ring A optionally bears 1 or 2 substituents selected from halogeno and (1–4C)alkyl substituents (especially fluoro, chloro, bromo, methyl and ethyl substituents) located in the 5'-, 6'- or 7'- position.

The preparation of the required enantiomeric forms of the compounds of formula I from synthetic samples of the corresponding racemic form is decribed in European patent application Publication No. 28906A(1)and in the Examples hereinafter.

The process may be carried out by heating a single enantiomer (or a mixture of both enantiomers in which one predominates over the other) alone or, more conveniently, in the presence of one or more inert diluents or solvents of relatively high boiling point. Examples of suitable diluents or solvents are 2-ethoxyethanol, 2-(2-methoxyethoxy)ethanol, xylene, toluene, liquid paraffin, dichlorobenzene, N-methyl-2-pyrrolidone and N,N-dimethylformamide. One preferred solvent is, for example, N,N-dimethylformamide which may conveniently be used together with a suitable diluent such as xylene or toluene.

When a solvent or diluent is employed, a particularly suitable temperature is, for example, in the range 90° to 160° C., especially in the range 90° to 130° C. When no solvent or diluent is used a higher temperature must generally be employed, for example in the range 150° to 260° C.

The desired racemic form may be separated from the reaction mixture either by cooling, or by evaporation of the inert diluent or solvent, or by other conventional means. The extent of conversion to the racemic form may be assessed by measurement of the fall in optical rotation, change in melting point, or by other conventional means.

The process of the invention is of particular value in enabling mixtures containing an excess of an unwanted enantiomer over the desired enantiomer to be recycled to obtain the desired enantiomer. Such mixtures are obtained, for example, during the resolution of the racemic form of a compound of the formula I. Thus, after partial removal of one enantiomeric form of a compound of formula I by fractional crystallisation of its salt with a single enantiomeric form of an optically active quaternary ammonium base, the mother liquors become enriched in the other enantiomeric form of the compound of formula I. This mixture of enantiomers, after conventional work-up, for example acidification and filtration of the precipitated material or evaporation of the mother liquor, can then be racemised by the process of the invention and the racemic form recycled in the resolution process.

Accordingly, the invention also provides an improved process for the manufacture of an enantiomeric form of a compound of formula I which comprises:

(a) forming a diastereoisomeric mixture of salts between a racemic form of said compound and an optically active form of a suitable quaternary ammonium base;

(b) separating the mixture of salts obtained in (a) by fractional crystallisation from a suitable solvent to give a crystalline salt and a mother liquor;

(c) liberating the required enantiomeric forms of the compound of formula I from the crystalline salt obtained in (b) by acidification;

(d) liberating the mixture of enantiomeric forms of the compound of formula I by acidification of the salts in the mother liquor obtained in (b);

(e) heating the mixture of enantiomeric forms of the compound of formula I obtained in (d) at a temperature in the range 80° to 280° C., to give the racemic form of said compound; and (f) recycling the racemic form obtained in (e) in the salt formation step (a).

A suitable method for the formation of the salt in (a) is, for example, reacting a suitable quaternary ammonium base [such as an optically active form of N,N,N-trimethyl(1-phenylethyl)ammonium hydroxide or methoxide, or of N,N,N-trimethyl(2-hydroxy-1-methyl-2-phenylethyl)ammonium hydroxide or methoxide] with the racemic form of a compound of formula I. Alternatively, an alkali metal or alkaline earth metal salt (such as a sodium, potassium or calcium salt) of the racemic form of a compund of formula I may be reacted with a suitable quaternary ammonium halide (such as the chloride, bromide or iodide salt corresponding to either of the above quaternary ammonium hydroxides).

The process of the invention is illustrated by the following non-limiting Examples, in which, unless otherwise stated:

(i) all evaporations were carried out by rotary evaporation under reduced pressure;

(ii) all operations were carried out at room temperature that is at a temperature in the range 18° to 26° C.; and (iii) yields are given for illustration only.

EXAMPLE 1

A solution of (+)-1'-(3,4-dichlorobenzyl)-7'-fluoro-spiro[imidazolidine-4,3'-indoline]-2,2 ', 5-trione (2.0 g.) in N,N-dimethylformamide (100 ml.) was heated at 95°–100° C. The initial solution had an optical rotation of +0.896° at 589 nm and +4.865 at 365 nm (in a 10 cm length cell) at 23° C. This rotation fell to +0.536° at 589 nm and +2.909° at 365 nm after heating for 6 hours. After a further 24 hours heating, the rotation fell to zero at both 589 and 365 nm. [In all cases the rotations were measured at 23° C.] The cooled solution was then diluted with water (200 ml.), adjusted to pH 4 with 2 M hydrochloric acid and cooled to 0°–5° C. The crystalline precipitate which formed was collected and recrystallised from aqueous ethanol to give (+)-1'-(3,4-dichlorobenzyl)-7'-fluoro-spiro-[imidazolidine-4,3'indoline]-2,2',5-trione (0.9 g.), m.p. 248°–250° C.; $[\alpha]_D^{23}\ 0°$ (c=0.874, MeOH). [Note: Sodium D spectral line=589 nm].

The starting (+) enantiomer was obtained as a solid, m.p. 160°–162° C. (recrystallised from ethanol), $[\alpha]_D^{\leq}+33.8°$ (c=1.0, EtOH), using an analogous procedure to that described in European patent application, publication No. 28906A(1), that is by resolution of the racemic form by formation of the diastereoisomeric mixture of salts with (−)-N,N,N-trimethyl(1-phenylethyl) ammonium hydroxide, followed by fractional crystallisation of a single diastereoisomeric salt and liberation of the enantiomeric form by acidification with hydrochloric acid. The diastereoisomeric salt had m.p. 171°–173° C. (crystallised from acetonitrile) and $[\alpha]_D^{23}+25.3°$ (c=1.0, EtOH).

EXAMPLES 2–4

The procedure described in Example 1 may be repeated using:

(Example 2): the (−)-enantiomer of 1'-(3,4-dichlorobenzyl)-7'-fluoro-spiro[imidazolidine- 4,3'-indoline]-2,2',5-trione ($[\alpha]_D^{23}$ −32°[EtOH]; m.p. 165° C. [recrystallised from ethyl acetate/petrol ether b.p. 60°–80° C.], obtained as described in Example 1 but from the diastereoisomeric salt with (+)-N,N,N-trimethyl(1-phenylethyl)ammonium hydroxide, said salt having m.p. 170° C. (recrystallised from 2-propanol) and $[\alpha]_D^{23}$−24° [EtOH], to obtain the corresponding racemate m.p. 247°–250° C., $[\alpha]_D^{23}$ 0° (MeOH);

(Example 3): the (+)- enantiomer of 1'-(3,4-dichlorobenzyl)-spiro[ imidazolidine-4,3'-indoline]-2,2', 5-trione ($[\alpha]_D^{23}+41°$ [c, 1.6; MeOH]; m.p. 199°–200° C., obtained as described in European patent application, Publication No. 28906A1; or (Example 4): the (−)-enantiomer of 1'-(3,4-dichlorobenzyl)-spiro[imidazolidine-4,3'-indoline]-2,2', 5-trione $[\alpha]_D^{23}$−39.8° (acetone); m.p. 201°–202° C., obtained by an analogous procedure to that described in Example 1 from the diastereoisomeric salt with (+)-N,N,N-trimethyl(1-phenylethyl)ammonium hydroxide, said salt having m.p. 147°–149° C. [recrystallised from 2-propanol and then acetonitrile] and $[\alpha]_D^{23}$−32.6° (MeOH); to obtain in either case the racemic form of 1'-(3,4-dichlorobenzyl)-spiro[imidazolidine 4,3'-indoline]-2,2', 5-trione, m.p. 269°–271° C., $[\alpha]_D^{23}$ 0° (MeOH).

[Note: the concentrations used for $[\alpha]_D$ determinations were approximately 1.0 g.per 100 ml. of solvent i.e. c=1.0].

EXAMPLE 5

A mixture of solid (+)-1'-(3,4-dichlorobenzyl)-spiro[imidazolidine-4,3'indoline]-2,2', 5-trione (5 g.) with liquid paraffin (40 ml.) was warmed to 200°–210° C. The solid melted initially and then resolidified. The mixture was then heated at 210°–220° C. for 30 minutes, cooled to 20°–25° C., diluted with toluene and the solid material collected by filtration, washed with toluene and recrystallised from ethyl acetate/petrol ether b.p. 60°-80° C. There was thus obtained the racemic form of 1'-(3,4-dichlorobenzyl)-spiro[imidazolidine-4,3'-indoline]-2,2', 5-trione; $[\alpha]_D^{24}$ 0° (MeOH, c=1.0).

EXAMPLE 6

A solution of (+)-1'-(4-bromo-2-fluorobenzyl)-7'-chloro-spiro[imidazolidine-4,3'-indoline)-2,2', 5-trione (103 mg., m.p. 260°-262° C. $[\alpha]_D^{24}$+17.9°, c=1.01, MeOH) in N,N-dimethylformamide (DMF) (1 ml.) was heated at 110° C. for 20 hours. The solution was diluted with water (20 ml.) and made acid with dilute hydrochloric acid. The precipitate was collected and recrystallised from methanol to give the racemic form of 1'-(4-bromo-2-fluorobenzyl)-7'-chloro-spiro[imidazolidine-4,3'-indoline]-2,2', 5-trione (60 mg.), m.p. 240°-241°; $[\alpha]_D^{23}$ 0.02° (c=0.92, MeOH).

EXAMPLE 7

The procedure described in Example 6 was repeated using the (−)-enantiomer of 1'-(4-bromo-2fluorobenzyl)-7'-chloro-spiro[imidazolidine-4,3'indoline]-2,2', 5-trione ($[\alpha]_D^{23}$−18.4, c=1.06, MeOH) to obtain the corresponding racemic form, m.p. 240°-241° C. $[\alpha]_D^{24}$ 0.01° (c =1.01, MeOH).

The enantiomers required for Examples 6 and 7 were obtained as follows:

Racemic 1'-(4-bromo-2-fluorobenzyl)-7'-chloro-spiro[imidazolidine-4,3'-indoline]-2,2', 5-trione (64.4 g.) was dissolved in a 9.253 M solution of (−)-N,N,N-trimethyl(1-phenylethyl)ammonium hydroxide in methanol (581 ml.). The solution was filtered and the filtrate was evaporated. The residue was dissolved in 2-methoxyethanol (132 ml.). The solution was warmed to 70° C. and then diluted with 1,2-dimethoxyethane (440 ml.) previously warmed to 70° C. The clear solution was stored at 0° C. for 48 hours and the crystals of the quaternary ammonium salt (A) were collected by filtration [27 g.; $[\alpha]_D^{23}$+21.1°, c=0.93,MeOH)]. This product was recrystallised from 2-methoxyethanol (55.3 ml.) and 1,2-dimethoxyethane (184 ml.) to give crystals [20 g.; $[\alpha]_D^{23}$+22° c=1.11, MeOH)].

A third recrystallisation gave crystals [15.8 g.; $[\alpha]_D^{24}$+21.9° c=1.12 MeOH)].

The crystalline salt (15.8 g.) thus obtained was dissolved in methanol (50 ml.) and treated with 0.25 M aqueous hydrochloric acid (105 ml.). The solution was chilled at 0° C. overnight and the solid removed by filtration, washed with water and dried over phosphorous pentoxide under vaccuum to give the (+)-enantiomer of 1'-[4-bromo-2-fluorobenzyl]-7'-chlorospiro(imidazolidine-4,3'-indoline)-2,2', 5-trione (9.1 g. , m.p. 260°-262° C., $[\alpha]_D^{23}$+17.9 (c=0.89, MeOH).

The mother liquors which were obtained after isolation of the salt A were diluted with ether (600 ml.) The precipitate was removed by filtration, washed with ether and dried. The solid obtained [31.5 g., $[\alpha]_D^{23}$−25.3° c=1.01, MeOH)] was dissolved in methanol (100 ml.). The solution was acidified with 2 M hydrochloric acid (200 ml.). The precipitate was collected by filtration washed with water and air dried to give solid (B)* [21.8 g.; $[\alpha]_D^{23}$−12.3° (c=0.95 MeOH)] containing principally the (−)-enantiomer of 1'-(4-bromo-2-fluoro-benzyl)-7'-chloro-spiro(imidazolidine-4,3'-indoline)-2,2', 5-trione. Solid B (21.5 g.) was dissolved in a 0.412 M solution of (+)-N,N,N-trimethyl(1-phenylethyl)ammonium hydroxide in methanol (116 ml.). The solution was evaporated and the residue dissolved in 2-methoxyethanol (43 ml.) at 70° C. 1,2-Dimethoxyethane (152 ml.) was added to the hot solution which was then cooled. The crystalline salt which formed, was collected by filtration [yield 17.0 g.; $[\alpha]_D^{23}$−23.5° (c=0.68 MeOH)] and recrystallised from a 1:3 v/v mixture (65 ml.) of 2-methoxyethanol and 1,2-dimethoxyethane to give a crystalline salt (C) [14.6 g.; $[\alpha]_D^{23}$−22.9° (c=1.06 MeOH)]. The salt (C) was dissolved in methanol (50 ml.) and the solution acidified with 0.25 M hydrochloric acid (105 ml.). This mixture was then cooled at 0°-5° C. for 16 hours and the solid which had deposited was collected by filtration, washed with water, dried and recrystallised from ethanol to give the (−)-enantiomer of 1'-(4-bromo-2-fluorobenzyl)-7'-chloro-spiro(imidazolidine-4,3'-indoline]-2,2', 5-trione, as a solid (8.0 g.); $[\alpha]_D^{23}$−18.4° (c=1.06, MeOH).

*Solid B may be converted to the corresponding racemate by heating in DMF at 110°-120° C. for 24 hours and working up as described for the racemate in Example 6.

The racemic starting material was obtained as follows:

A suspension of 7-chloroindoline-2,3-dione (15g.) and potassium carbonate (15 g.) in N,N-dimethylformamide (100 ml.) was stirred and treated with a solution of 4-bromo-2-fluorobenzyl bromide (24.7 g.) in chlorobenzene (100 ml.). The mixture was stirred at 90° C. for five hours, cooled to ambient temperature, and diluted with a mixture of water (500 ml.) and petrol ether (b.p 60°-80° C.) (500 ml). The aqueous phase was adjusted to pH3 with 10 M hydrochloric acid. The mixture obtained was separated by filtration. The solid obtained was washed with further petrol ether, then with water, and recrystallised from ethanol to give 1-(4-bromo-2-fluorobenzyl)-7- chloro-indoline-2,3-dione (15.5 g.), m.p. 164°-166° C.

A stirred suspension of 1-(4-bromo-2-fluorobenzyl)-7-chloro-indoline-2,3-dione (96 g.) in ethanol (1500 ml.) was treated with a solution of potassium cyanide (21.0 g.) and ammonium carbonate (300 g.) in water (1500 ml.). The mixture was stirred at 45°-50° C. for 4 hours. Activated charcoal (50 g.) was added and the mixture was stirred for a further hour at 45°-50° C. The hot mixture was filtered through diatomaceous earth and the filter cake was washed with aqueous ethanol (2×200 ml.; 1:1 v/v) at 60° C. The cooled filtrate was made acid to pH 4 at 0°-5° C. with 10 M hydrochloric acid and the precipitated solid was collected by filtration, washed with water and dried. Recrystallisation twice from 1:1 v/v ethyl acetate/petroleum ether, b.p. 60°-80° C. gave (+)-1'-(4-bromo-2-fluoro-benzyl)-7'-chloro-spiro(imidazolidine-4,3'-indoline)2,2', 5-trione (60 g.) m.p. 240°-242° C.

EXAMPLE 8

The procedure described in Example 4 was repeated except that the reaction solution was heated at 135°-140° C. for 30 hours, to yield to racemic form of 1'-(3,4-dichlorobenzyl)-spiro[imidazolidine-4,3'-indoline]-2,2', 5-trione (0.58 g.), m.p. 270°-271° C., $[\alpha]_D^{24}$ 0° (c=1.01 (MeOH), starting from the corresponding (−)-enantiomer (1.05 g.). After 16 hours of heating partial racemistaion had occurred as indicated by the specific rotation ($[\alpha]_D^{24}$−4°, (c=1.2 MeOH) of a sample worked up and isolated after 16 hours.

EXAMPLE 9

A solution of (+)-1'-(4-bromo-2-fluorobenzyl)7-methyl-spiro[pyrrolidine-3,3'-indoline]-2,2', 5-trione [1.42 g.; m.p. 231°-231°, $[\alpha]_D^{24}+18.4°$ (c=0.95,DMF)] in DMF (10 ml.) was heated at 110° C. for 16 hours. The solution was diluted with water (50 ml.), acidified with dilute hydrochloric acid and extracted with ethyl acetate (3×50 ml.). The combined extracts were evaporated. The residual gum was recrystallised from ethyl acetate to give (+)-1'-(4-bromo-2-fluorobenzyl)-7-methyl-spiro[pyrrolidine-3,3'-indoline]-2,2', 5-trione (426 mg.) m.p. 215°-216°; $[\alpha]_D^{23}$ 0.0 (c=1.12, DMF).

Essentially the same result was obtained starting from the (−)-enantiomer [m.p. 230°-232° C; $[\alpha]_D^{24}-18.3°$ (c=1.06, DMF)].

The starting enantiomers may be obtained from the racemate, for example, by an analogous resolution procedure to that described in Example 7 using N-methyl-cinchonidinium hydroxide in place of N,N,N-trimethyl(1-phenylethyl)ammonium hydroxide (TPAH) to obtain the (+) enantiomer and using N-methyl-quinidinium hydroxide in place of TPAH to obtain the (−)-enantiomer.

In either case, the mixture of enantiomers left in the mother liquors after separation of the crystalline salt formed with the quaternary ammonium hydroxide, may be isolated by acidification and converted to give further racemate by heating in DMF as described above.

The necessary quaternary ammonium hydroxides may be made by reacting cinchonidine or quinidine in acetone with excess methyl iodide and potassium carbonate in acetone to give the corresponding quaternary ammonium iodide after conventional work-up. This iodide is then converted to the corresponding hydroxide by dissolving the solid iodide in water and passing the solution through a column of anion exchanging resin (such as "Amberlite" [Trade-mark] IRA401) newly converted into the hydroxide form using methanol as eluant.

EXAMPLE 10

Using an analogous procedure to that described in Example 6, but starting with the (+)-enantiomer of 1'-(3,4-dichlorobenzyl)-spiro[pyrrolidine-3,3'-indoline]-2,2', 5-trione [100 mg.; m.p. 240°-242° C., $[\alpha]_D^{23}+26.6°$ (c=0.96, DMF)], there was obtained the racemic form of 1'-(3,4-dichlorobenzyl)-spiro[pyrrolidine-3,3'-indoline]-2,2', 5-trione (64 mg.), m.p. 210°-212° C. (recrystallised from methanol), $[\alpha]_D^{22}$ 0° (c=1.0, DMF).

The necessary (+)-enantiomer was obtained by resolution of the corresponding racemate using the (−)-enantiomer of N,N,N-trimethyl-(2-hydroxy-1-methyl-2phenylethyl)ammonium hydroxide as the resolving base. The latter material may be obtained by reacting (−)-ephedrine with methyl iodide and potassium carbonate in acetone to give the corresponding quaternary ammonium iodide salt (m.p. 210°-212° C.), recrystallised from a mixture of methanol and ether, which is then converted to the corresponding hydroxide by treatment with anion exchanging resin in hydroxide form as described in Example 9.

The mixture of enantiomers [enriched in the (−)-enantiomer] left after separation of the crystalline salt with the quaternary ammonium hydroxide, may be isolated by acidification and converted to give further racemate by heating in DMF as described above.

EXAMPLE 11

Using a similar procedure to that described in Example 6, but starting from the (+)-enantiomer of 1'-(4-bromo-2-fluorobenzyl)-7'-fluoro-spiro[pyrrolidine-3,3'-indoline]-2,2', 5-trione [m.p. 193°-194° C.; $[\alpha]_D^{24}+7.5°$ (c=1.0, tetrahydrofuran)], the corresponding racemate may be obtained of m.p. 240°-242° C., $[\alpha]_D^{23}$ 0° (c=0.95, MeOH).

The required (+)-enantiomer may be obtained by resolution of the racemate using(−)-N-(methyl)-cinchonidinium hydroxide as the resolving base.

Again, as in previous Examples the mixture of enantiomers [enriched in (−)-enantiomer] obtained after separation of the crystalline salt with the resolving base, may be isolated by acidification and converted to give further racemate by heating in DMF as described above.

EXAMPLE 12

A mixture of (+)- and (−)- enantiomers of 1'-(3,4-dichlorobenzyl)-7'-fluoro-spiro[imidazolidine-4,3'-indoline]-2,2', 5-trione [1.0 g.; $[\alpha]_D^{24}-11.7°$ -(c=1.0, MeOH)] was suspended in 1,2-dichlorobenzene (10 ml.) and the mixture was heated at 135°-140° C. for sixteen hours. Complete solution did not occur. The mixture was cooled to ambient temperature. The solid was separated by filtration and washed with ether to give (+)-1'-(3,4-dichlorobenzyl)-7'-fluoro-spiro-[imidazolidine-4,3'-indoline]-2,2', 5-trione (676 mg.), m.p. 246° C., $[\alpha]_D^{24}-0.01°$ (c=1.2,MeOH).

A similar result may be obtained using N-methyl-2-pyrrolidinone as solvent except that complete solution occurs and the racemate is isolated by adding the solution to an excess of water.

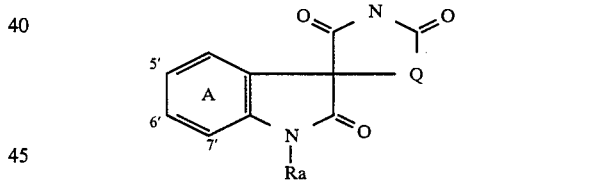

Formula I

What is claimed is:

1. A process for the manufacture of a compound of the formula I

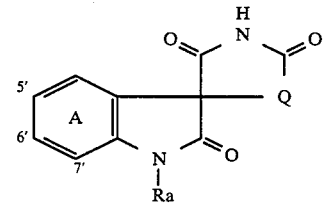

in racemic form, wherein Ra is (2-12C)alkyl, or naphthylmethyl or cinnamyl optionally bearing one or two halogeno substituents, or benzyl optionally bearing one or two substituents independently selected from halogen, (1-4C)alkyl, (1-4C)alkoxy, cyano, nitro and trifluoromethyl located in the 2-, 3-, 4- or 5-position of the phenyl moiety; benzene ring A optionally bears one or two substituents independently selected from halogeno, (1–4C)alkyl, trifluoromethyl and nitro; and Q is methylene or imino; but Ra is other than ethyl, n-propyl or unsubstituted benzyl when benzene ring A is unsubstituted and Q is imino; characterised by heating an enantiomeric form of the compound of formula I; or a mixture of both enantiomeric forms of said compound containing an excess of one enantiomeric form over the other; at a temperature in the range 80° to 280° C.

2. A process according to claim 1 wherein in the starting material Ra is a propyl, butyl, pentyl, hexyl, heptyl, 1-naphthylmethyl, 2-naphthylmethyl, cinnamyl, halogenocinnamyl, dihalogenocinnamyl, benzyl, (1–4C)-alkylbenzyl, trifluoromethyl-, halogeno-benzyl or dihalogenobenzyl; benzyl ring A is unsubstituted or bears a fluoro, chloro, bromo, methyl or trifluoromethyl substituent located at the 5'-, 6'- or 7'-position; and Q is imino or methylene.

3. A process according to claim 1 wherein in the starting material Ra is dihalogenobenzyl and benzene ring A bears 1 or 2 substituents selected from halogeno and (1–4C)alkyl substituents located at the 5'-, 6'- or 7'-position.

4. A process according to claim 1 wherein in the starting material Ra is 2,4-dichlorobenzyl, 4-chloro-2-fluorobenzyl, 4-bromo-2-fluorobenzyl, 2-fluoro-4-iodobenzyl, 3,4-dichlorobenzyl, 3-bromo-4-chlorobenzyl or 4-bromo-3-chlorobenzyl, and benzene ring A bears 1 or 2 substituents selected from fluoro, chloro, bromo, methyl and ethyl substituents located in the 5'-, 6'- or 7'-position.

5. A process according to any of claims 1–4 chracterised in that it is performed in the absence of a solvent or diluent at a temperature in the range 150°–280° C.

6. A process according to any of claims 1–4 characterised in that it is performed in the presence of a solvent or diluent.

7. A process according to claim 6 characterised in that the solvent or diluent is selected from 2-ethoxyethanol, 2-(2-methoxyethoxy)ethanol, xylene, toluene, liquid paraffin, dichlorobenzene, N-methyl-2-pyrrolidone and N,N-dimethylformamide.

8. A process according to claim 6 characterised in that the solvent or diluent is N,N-dimethylformamide optionally together with toluene or xylene.

9. A process according to any of claims 6–8 characterised in that it is performed at a temperature in the range 90° to 130° C.

* * * * *